United States Patent
Henze et al.

(10) Patent No.: US 9,404,921 B2
(45) Date of Patent: Aug. 2, 2016

(54) PROCESS FOR DETECTING CELLS FROM A SAMPLE

(75) Inventors: Stephan Henze, Erfurt (DE); Peter Miethe, Schleberoda (DE)

(73) Assignee: FZMB GMBH FORSCHUNGZENTRUM FUER MEDIZINTECHNIK UND BIOTECHNOLOGIE, Bad Langensalze (DE)

( * ) Notice: Subject to any disclaimer, the term of this patent is extended or adjusted under 35 U.S.C. 154(b) by 0 days.

(21) Appl. No.: 13/982,796

(22) PCT Filed: Feb. 10, 2012

(86) PCT No.: PCT/EP2012/052316
§ 371 (c)(1),
(2), (4) Date: Sep. 9, 2013

(87) PCT Pub. No.: WO2012/107559
PCT Pub. Date: Aug. 16, 2012

(65) Prior Publication Data
US 2013/0337437 A1    Dec. 19, 2013

Related U.S. Application Data

(60) Provisional application No. 61/441,773, filed on Feb. 11, 2011.

(30) Foreign Application Priority Data

Feb. 11, 2011  (EP) ..................................... 11154137

(51) Int. Cl.
*G01N 33/569* (2006.01)
*G01N 33/543* (2006.01)

(52) U.S. Cl.
CPC ...... *G01N 33/56911* (2013.01); *G01N 33/5436* (2013.01); *G01N 33/54313* (2013.01); *G01N 33/54366* (2013.01); *G01N 33/54386* (2013.01); *G01N 33/569* (2013.01)

(58) Field of Classification Search
CPC .................. G01N 33/56911; G01N 33/54366; G01N 33/5436; G01N 33/569; G01N 33/54386; G01N 33/54313
See application file for complete search history.

(56) References Cited

U.S. PATENT DOCUMENTS

| | | | |
|---|---|---|---|
| 4,727,019 A * | 2/1988 | Valkirs et al. | 435/5 |
| 5,321,545 A * | 6/1994 | Bisconte | 359/391 |
| 2013/0244225 A1 * | 9/2013 | Kshirsagar et al. | 435/5 |

FOREIGN PATENT DOCUMENTS

| | | | |
|---|---|---|---|
| DE | 10 2007 025 311 | 12/2008 | |
| EP | 0 421 235 | 4/1991 | |
| EP | 2 317 319 | 5/2001 | |
| EP | 1 223 429 | 7/2002 | |
| WO | 85/05451 | 12/1985 | |
| WO | 91/01485 | 2/1991 | |
| WO | 2004/072097 | 8/2004 | |
| WO | 2008/118400 | 10/2008 | |
| WO | WO 2008/145722 * | 12/2008 | ........... G01N 33/538 |

\* cited by examiner

*Primary Examiner* — Gail R Gabel
(74) *Attorney, Agent, or Firm* — Jacobson Holman PLLC

(57) ABSTRACT

A process for detecting cells involves applying a liquid, cell-containing sample to a porous support so that the cells enter the support pores and are retained by a cell-specific binding molecule on the pore surface and, optionally after the cells are detectably labeled, performing an optical read-out by high density imaging the entire porous support volume using an optical system having an optical axis that runs in the direction of sample flow.

17 Claims, 4 Drawing Sheets

PROCESS FOR DETECTING CELLS FROM A SAMPLE

This is a 371 of PCT/EP12/052316 filed Feb. 10, 2012, which has a priority of European no. 11154137.1, filed Feb. 11, 2011, U.S. provisional application No. 61/441,773, filed Feb. 11, 2011, hereby incorporated by reference.

The present invention relates to a process for detecting cells, especially of microorganisms, from a sample.

The quantitative and qualitative detection of cells in complex sample solutions is a basic operation in microbiology, cytology and modern biotechnology.

In this context, the quick and direct detection of microorganisms in food samples is particularly demanding. It makes high demands because of the possibly high complexity of the sample matrix and the requirement of ensuring sterility with respect to particularly relevant germs, such as *Salmonella*, *Listeria* or *Legionella* (drinking water), and thus the detection limit of a germ. In particular, the food industry asks for methods in which a step of enrichment, i.e., reproduction of the microorganisms, is not necessary. The provision of novel quick and inexpensive microbiological detection methods is a question of great practical relevance. Despite remarkable innovative scientific achievements for improving public health and animal health and despite the reduction of infectious diseases in recent decades, about three million humans die worldwide every year from the consequences of food-borne diseases. Thus, food-related infections are found on the same level as AIDS and even above tuberculosis in the cause of death statistics.

In the currently established examination methods in accordance with the requirements and recommendations of the German Food and Feed Act (LFGB, 2006), an aliquot of the food (usually 25 g) or an abrasive sponge sample or a sample punched out from the carcass surface as well as swabs is suspended in 225 ml of liquid medium, in order to increase the detection sensitivity for homogeneously and partially contaminated foods. With this method, bacteria are eluted into the medium on the one hand, and on the other hand, the medium serves to vitalize sublethally damaged bacteria for culture-dependent methods. This step is usually effected in one or more non-selective or selective preliminary enrichment steps that last several hours. The classical detection step is performed subsequently by plating the preliminary culture on a nutrient agar plate, assuming the paradigm that a colony is formed from each cell. Thus, for example, the pathogen to be detected is subjected to preliminary culture in one or more liquid selective enrichment media for 24 to 48 hours in the established microbiological meat examinations. After culturing on solid media (selective agar), the bacteria are evaluated morphologically and phenotypically. After passaging to an inhibitor-free agar, the isolates are ultimately characterized biochemically and serologically up to the level of eating. The whole course of the examination from the arrival of the sample in the laboratory to the statement of result, for example, for *Listeria monocytogenes*, takes three (negative sample) to five (positive sample) days.

For the realization of legislative requirements, which require a large number of additional in-process controls, especially without much delay, the previously employed technology is too slow and too complicated. In addition, all processes in which a specific enrichment/reproduction of the microorganisms takes place must be performed in a microbiological laboratory approved by the authorities (Section 64 of German Infection Protection Act). Food manufacturers usually shy away from the associated logistic and financial expenditure and ask for quick methods in order to avoid the problems mentioned.

Therefore, many attempts were made in the last two decades to develop quicker methods in which a detection can be performed without forming colonies after a non-selective preliminary enrichment, which may be shortened. These methods are briefly described in the following.

Nucleic acid detection method (PCR, RNA hybridization, NASBA): As a rule, this involves cell lysis with subsequent nucleic acid extraction, amplification of specific nucleic acid targets and final detection. With an average amount of template employed of 1-10 µl, detection limits of about 10 genome equivalents/sample can be reached. Since the sample volume employed is usually only 10-50 µl, germ numbers of $10^3$ to $10^4$ must be reached in several hours of preincubation in order that the sterility of the starting sample can be ascertained.

Immunoassays (ELISA, immunochromatography): This is based on the highly specific binding reaction of an antigen with its corresponding antibody with subsequent optical detection of the reaction product by the binding of an enzyme- or dye-labeled detection antibody to the previously formed complex. Immunoassays work with sample volumes of about 50-200 µl with detection limits of about $10^3$ to $10^4$ CFU/sample (ELISA) or $10^4$ to $10^5$ CFU/sample (immunochromatography). Several hours of preliminary enrichment steps are necessary here in order to achieve such germ numbers and be certain about the sterility of the starting sample.

Flow cytometry: Flow cytometry in combination with fluorescent conjugates and magnetic particles has been employed for food examinations. The detection limits are on the order of $10^3$ CFU/ml. Therefore, this method cannot be employed without preliminary enrichment either. In addition, flow cytometry is employed for the immunophenotyping of blood cells, especially leukocytes. Similar methodological disadvantages as when used in microbiology are seen here. About 5000 cells must be detected in order to achieve valid results. In the case of leukocytes, this results in very long measuring times because of the large excess of erythrocytes. To avoid this, a preliminary enrichment of the leukocytes to be measured, for example, by separating the leukocytes by means of centrifugation in a density gradient or by selective osmotic lysis of the erythrocytes is necessary here as well. These methods are tedious, in part not sufficiently selective, and lead to a loss of cells.

Antibody direct epifluorescent filter technique: In this technique, the separation of the microorganisms is effected on a surface filter by size exclusion. Typically, 0.45 µm filters are employed. The detection is usually effected by staining with vital stain (live/dead staining, see below), or alternatively by immunofluorescent conjugates. With this technique, detection limits within a range of 10-100 CFU/sample can be reached in principle. What is problematic is the high susceptibility to failure of the method because of particulate deposits of food components on the filter. Therefore, it can be employed only for relatively clean samples or after separation of corpuscular components, and because of its susceptibility to failure, it is practically limited to sample volumes within a range of from 1-10 ml.

In the patent literature, some specific designs for these platform techniques have been described. Thus, EP-A-1 223 429 describes a process for the detection of living microorganisms and/or eukaryotic cells, especially monocellular organisms, molds in samples, in which the samples in liquid form are contacted with a support having receptors specific for the microorganism(s) to be determined, said microorganism(s) is (are) bound to the receptors, and a factor that is indicative of living microorganisms is measured. The support in the process described therein includes material provided in a column in the form of a molded part, loose packings in particulate form, in the form of a gel or as a dispersion that carries at least one receptor for specifically binding the microorganism to be determined and is permeable to a fluid. The support material has a mean pore diameter of from 1 to 200 μm and a pore volume fraction of from 20 to 80%. The support material has no, or only a very low and non-specific, sorptivity for the microorganisms and has a load of $10^2$ to $10^{18}$ receptors per ml of support. The analyses are typically performed in microcolumns with cylindrical filter elements or packings, and the optical changes on the filter are detected integrally. The direction of flow and the direction of evaluation are perpendicular to each another. The process reaches similar detection limits as the above described immunoassay method.

WO-A-2008/118400 discloses the quick detection and identification of colonies of microorganisms grown on transparent permeable membranes. The detection is done on a conventional agar plate with a color indicator. This is an improved classical microbiological operating procedure, which allows a more efficient operation.

WO-A-2004/072097 discloses a microchip-based system for HIV diagnosis. A process variant described therein relates to the detection of cells on an antibody-coupled nucleopore membrane, the pores being smaller than the cells to be detected.

WO-A-91/01485 relates to a colorimetric or fluorimetric quick test with quantitative evaluation. For detecting cell components, the latter are extracted, and the detection of antigen is effected on a support bearing antibodies.

EP-A-0421235 discloses hydrophilic membranes laminated onto support structures for application in lateral flow strip tests.

WO-A-85/05451 describes sandwich assays performed on porous solid phases. The solid phase is passed axially when the assay is performed. The pores of the porous membranes are not specified. However, it appears that pore sizes are used that are smaller than the size of the cells to be examined.

EP-A-2317319 suggests a porous solid phase for a binding assay that enables a test sample such as whole blood to be analyzed promptly, conveniently, accurately, and inexpensively without requiring a pretreatment, and a binding assay method using said porous solid phase are disclosed. At least one surfactant is incorporated into the porous solid phase for binding assay prior to addition of a test sample, the at least one surfactant being selected from the group consisting of (A) a sugar-containing surfactant that comprises a compound shown by a general formula (I), (B) a sugar-containing surfactant that comprises a sucrose fatty acid ester wherein the constituent fatty acid has 5 to 14 carbon atoms, and (C) a steroid surfactant. The reference is silent with respect to the importance of penetration of the component to be analysed into the pores of the porous solid phase.

The object of the invention is to provide a test that indicates defined prokaryotic and eukaryotic cells. The test is to be simply and quickly performed and simply and inexpensively prepared. It should allow for the detection of cells, especially of microorganisms, even for small cell numbers on the order of <100 cells, especially on the order of <10 cells, and it should be usable in a wide variety of complex liquid samples. With this test, it should be possible to detect both living and dead cells. Thus, it should be possible to use the process in microbiology, but also in other fields of applications with analogous use characteristics, such as the detection of specific somatic cells in body fluids or cell cultures.

The object of the invention is achieved by a process for detecting cells from a sample, comprising the following steps:
(a) applying the sample or a fraction of the sample in liquid phase in a direction of flow to a porous, generally two-dimensional support with pores having on the surface thereof at least one binding molecule specific for the cells to be detected or of fragments of the cells to be detected;
(b) allowing the cells to be detected or the fragments of the cells to be detected to enter from the sample or sample fraction into the pores of said porous, generally two-dimensional support, said pores having such a mean pore size that the cells or fragments to be detected are able to enter into the pores;
(c) retaining the cells or fragments to be detected by at least one binding molecule specific for the cell to be detected; said sample support is optionally washed after the sample or fraction of sample has been applied and the cell to be detected or fragments of the cells to be detected have entered the pores;
(d) performing an optical read-out method on said substantially two-dimensional support by an imaging method, optionally after the cell to be detected or fragments of the cells to be detected have been labeled with a labeling agent; wherein
(e) the optical axis of an optical system comprising e.g. a lens system used for the read-out method generally runs in the direction of flow of the sample or the sample fraction; and
(f) the detection of the cell or of fragments of the cells to be detected is effected at the surface of said porous, generally two-dimensional support.

Figure 1:
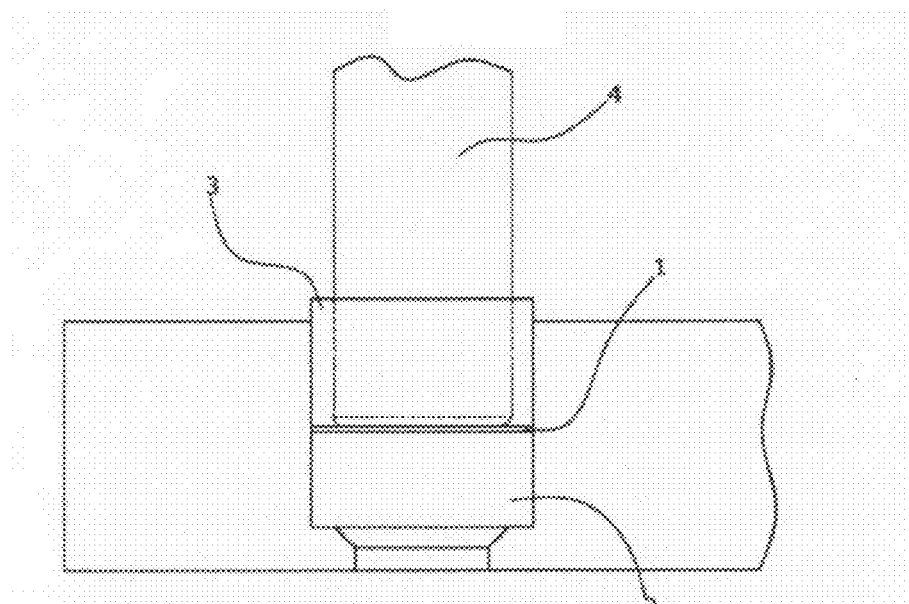
FIG. 1 schematically shows a device that can be employed in the process according to the invention.

Within the meaning of the present invention, "generally two-dimensional support" means a support having a thickness of 10 μm to 2 mm and length and width dimensions of 1 mm to 100 mm.

Specific binding molecules within the meaning of the present invention are the biological and synthetic ligands known from conventional binding assays and affinity chromatography, which undergo binding with the cells to be detected or with a binding molecule specific for the cells that has been added to the sample, with preference over other components of the sample. These include, in particular, natural or recombinant antibodies, antibody fragments and mimetics, immunologically active antigens, oligonucleotides, poly- and oligosaccharides, molecules binding poly- and oligosaccharides, such as lectins, ligands of cell membrane receptors, bacteriophages or phage proteins, IgG-binding proteins, such as protein G, A or L, and binding partners of specific affinity tags, such as Step tag, His tag and the like. In addition, ligands with hydrophobic, anionic, cationic or zwitterionic properties or with surface structures produced by molecular imprinting may also be employed if they allow for the at least partially selective binding of particular cells or classes of cells when the binding properties are appropriately selected. A typical example thereof is the binding of Gram negative microorganisms to weak anion exchangers. Further examples of binding molecules are found, for example, in Affinity Chromatography (2006), Vol. 92, Taylor & Francis, edited by David S. Hage.

Because of the binding of the cell to be detected or fragments of cells to be detected, a washing solution can be added in the direction of flow of the sample application liquid or against the direction of flow of the sample application liquid in the optional washing step.

In a particular embodiment of the invention, the sample is subjected to a sample treatment causing the cell or a cell component to be labeled, before or after its application to the porous, generally two-dimensional support. This may be effected, for example, by staining by means of a dye. Staining or labeling methods are known to the skilled person.

The generally two-dimensional support that may be used in the process according to the invention, for example, a porous membrane, especially with a layer thickness within a range of from 0.05 to 1 mm.

According to the invention, the evaluation of the analysis may be effected, for example, by an optical read-out method by an optical microscopic method suitable for detecting the cells or for labeling, for example, by means of epifluorescence microscopy for the detection of fluorophors or bright field microscopy for the detection of chromophors. In particular, usual microscopes having a lens system with a magnification between 2× and 40× and a digital camera can be used for this.

In particular, a microorganism that is relevant under the German Food and Feed Act can be detected by the process according to the invention. In particular, the microorganism may be selected from the group consisting of *Salmonella* spp., *Listeria* spp., *E. coli*, coliform germs, *Campylobacter* spp., *Bacillus cereus*, sulfite-reducing clostridia, coagulase-positive staphylococci.

According to the invention, the receptor specific for the cell to be detected or its fragment may be selected, in particular, from the group consisting of antibodies against the cell to be detected or its fragment, lectins, bacteriophages, and specific natural and recombinant ligands of cell membrane receptors. For the detection of a group of cells or their fragments, especially of microorganisms such as Gram-negative bacteria, simple chemical substances, especially amines, may also be used.

In one embodiment of the invention, the support may consist of foamed, sintered or fibrous inorganic or organic materials.

The binding molecules specific for the cell to be detected can be bound to the material of which the support is made by known chemical methods, as described in the Handbook of Affinity Chromatography (2006), Vol. 92, Taylor & Francis, edited by David S. Hage, pp. 49 ff. For example, if the binding molecule is attached to the support by covalent binding, a functional group present on the support is coupled with a functional group present on the binding molecule. This may be effected directly or indirectly, through so-called spacers, which are usually bifunctional molecules. If no functional groups are present on the surface of said foamed, sintered or fibrous inorganic or organic materials in sufficient numbers to provide the necessary density of binding molecules, the material of which the support is made can be functionalized by suitable methods. Suitable methods are available to the skilled person for this purpose.

When the supports that may be used in the process according to the invention are prepared, sintered polyethylene material, for example, may be the starting material. Appropriate fibrous materials could also be employed.

In contrast to the procedures according to the prior art, the size of the pores of the porous supports to be used in the process according to the invention is selected in such a way that the cells or fragments of cells can penetrate into the pores. Thus, the pore size can be selected, depending on the sample material and cell type to be detected, from 2 μm to 200 μm, especially from 10 μm to 100 μm, i.e., significantly greater than in a prior art detection method for the same cell type. Thus, for example, the pore size for detecting bacteria to be used in the process according to the invention is from 2 μm to 50 μm, and that for detecting eukaryotic cells is from 40 μm to 200 μm. In each case, the lower limit approximately can correspond to about double the diameter of the cells to be detected in order that penetration of the cells into the support is possible. Supports having pore diameters of from 5 μm to 25 μm for detecting bacteria and from 40 μm to 100 μm for detecting eukaryotic cells have proven particularly advantageous.

Because of the pore diameters employed, the process according to the invention enables a highly effective prefiltration of the sample by means of a size-exclusion filter whose exclusion threshold is above the size of the cells to be detected, but below the pore size of the support according to the invention. Thus, solids that are still present in a thus prefiltrated sample, except for the cells to be detected, can pass the support unhindered. This reduces the probability of the filter becoming clogged, and accordingly increases the maximum filterable volume significantly over that of the prior art.

Typically, the pore size is within a range of from 2 μm to 100 μm, especially from 10 μm to 40 μm. Then, covalent binding of the binding molecules can be effected by chemically coupling them to suitable functional groups of the surface or by non-covalent adsorption to the surface. In addition to the binding properties of the filters, their optical properties and filtration properties as well as the compatibility of the material with the microbial agent are essential for the use of the support in the desired case of application.

It may be advantageous to render the cell or its fragment detectable by staining, even though the cell or its fragment may also be recognized by direct microscopic observation in principle. The cell to be detected or its fragment can be rendered detectable by a conjugate consisting of an antibody and an enzyme or an antibody and a dye or colorant particle, or by a nucleic acid probe consisting of an oligonucleotide and a dye, or an enzyme, an intercalation dye, or by means of an enzymatic reaction.

The following staining techniques can be employed in the process according to the invention:

Live/dead staining methods with dyes and fluorescent dyes: This is based on the dynamic incorporation of the dye as a labeling agent into the cell membrane or cell organelles, or conversion of a dye precursor by cell enzymes or by detecting intermediates of the respiratory chain, or by intercalation in DNA or RNA. Suitable dyes and their application protocols are known to the skilled person and documented, for example, in the Molecular Probes Handbook, A Guide to Fluorescent Probes and Labeling Technologies.

Immunostaining by means of antibody conjugates: Antibody-dye conjugates can be produced by coupling an antibody with a dye molecule or colorant particle. A broad range of chemically activated and activatable dyes exists for this purpose.

Antibody-enzyme conjugates are usually prepared by coupling the antibodies with horse radish peroxidase, galactose oxidase, or phosphatase. If microorganisms bound to the two-dimensional support are labeled with such conjugates, they can be made visible simply by adding a precipitating substrate based on tetramethyl-benzidine or a protein-binding substrate based on (E)-2-(2-[4-hydroxyphenyl]-vinyl)-3-ethyl-1,3-benzothiazolium iodide. Further suitable substrates are well known from biochemistry and immunohistochemistry.

In-situ hybridization: The intracellular labeling of specific DNA/RNA sequences with enzyme- or dye-labeled RNA has become established for the detection of microorganisms, for example, in microtitration plates. Suitable probes are commercially available for many microorganisms, and can be synthesized also for other cell types by known methods. The methods are easily adapted to membranes.

In particular, dyes that can be excited with simple solid light sources and dyes that exhibit a Stokes shift of more than 50 nm may be employed in these labeling techniques.

The method to be selected for reading out the porous, generally two-dimensional support can be determined by the labeling agent or by intrinsic properties of the cell. Possible evaluation methods for the process according to the invention include, for example, bright field or dark field microscopy in incident light or transmitted light technique, phase contrast and polarization contrast microscopy as well as fluorescence-microscopic methods, such as epifluorescence microscopy, confocal microscopy, fluorescence lifetime imaging spectroscopy, near-infrared spectroscopy imaging, multiphoton imaging. In particular, usual upright and inverted microscopes, for example, from the company Zeiss, can be used for this purpose.

Two-dimensional supports are to be employed, wherein said supports have surface areas of 1 mm$^2$ to 100 cm$^2$ with thicknesses of 10 μm to 2 mm to allow for detection of fluorescent cells in the support. Immersion fluids may optionally be employed for improving the optical properties. It is also possible to employ large area supports with a surface area within a range of up to 200 cm$^2$, and to apply the sample to be examined through a nozzle with a device like the spiral plater, which has become established in microbiology. It leaves a trace, which can be retraced and evaluated with an optical means.

The process according to the invention enables the sought cells to be retained in the entire volume of the support according to the invention. A high definition image of the entire support volume, which includes the whole thickness of the support, in particular, is advantageous to completely detect the retained cells. According to the invention, this can be achieved by mechanical, image-processing and optical measures. For example, when applying the method, the focal plane of a microscope can be shifted through the entire thickness of the support when a support is visually inspected. Also, in digital image acquisition, a focus stack, i.e., a collection of images with the same picture detail, but different focal planes, can be prepared, and a high definition image of all objects in the entire dimension of the stack can be calculated therefrom. Suitable algorithms for this are per se known to the skilled person. In particular, the addition of all the images of a focus stack of fluorescence micrographs pixel by pixel has proven useful. If the objects to be imaged are greater than 10 μm, for example, eukaryotic cells or color halos of an enzyme dye substrate reaction, the required depth of field can be achieved by using an objective with a low magnification and numerical aperture. In particular, these are objectives with magnifications of from 0.5× to 5× and numerical apertures of from 0.01 to 0.1. In addition, light field microscopy and digital holography may also be used as image acquisition methods.

Particularly inexpensive optical evaluation units can be realized with a digital camera. The imaging can be effected directly by placing the membrane onto an image sensor with a pixel pitch of 0.1 to 2 μm. Also, a conventional imaging system can be used by combining the camera with a macro lens, or a microscope objective and tube. In both cases, the evaluation can be effected simply on a computer screen or by methods of electronic image processing. With such systems, images with a spatial resolution of 2 to 0.5 μm per pixel with a magnification of up to 400 times, which is well suited for screening tests, can be produced with little technical expenditure. In particular, the optical system may be realized by a usual USB microscope.

It can improve the sensitivity of the process according to the invention if the difference between the indices of refraction, $n_r$-$n_p$, of the medium filling the pores of the porous, generally two-dimensional support, $n_p$, and that of the porous, generally two-dimensional support, $n_r$, is smaller than 0.05, especially smaller than 0.02.

An approximation of the refractive indices of the pores and solid phase can be achieved if the pore is filled with a liquid whose refractive index is similar to that of the solid phase. This can be done by suitably selecting the reagents used in the assay, or by exchanging the content of the pores after a binding assay has been completed.

In a first case, an assay reagent can be admixed, for example with a substance increasing its refractive index that is miscible with water or soluble in water, at a concentration that approximates the refractive index of the mixture to that of the solid phase. Particularly suitable mixing partners are water-miscible liquids of high density, such as glycerol, short-chain polyethylene glycols, thiodiglycol. Suitable soluble substances are those having a high solubility and high molecular weight, such as sodium iodide, cesium chloride, or sucrose. The concentration of the added substances should remain so low that the assay, for example, the formation of antibody complexes, is not impeded.

In another case, the last added assay reagent can be displaced, in the course of or after completion of the binding assay, by a liquid whose refractive index is the same as that of the solid phase. For this purpose, the same aqueous mixtures and solutions as described in the previous paragraph are suitable, first of all. However, the concentration at which the substance can be added is less restricted. In some cases, the formation of immune complexes may even be prevented. However, the binding of immune complexes that have already been formed should be maintained. Especially when thiodiglycol is used, the substance can be used in a pure form, whereby even the refractive indices of conventional solid phases, such as nitrocellulose, can be achieved. If the solid phase is sufficiently wettable, substances that are immiscible with water, such as immersion oils, may also be used.

In one embodiment, the support that can be employed in the process according to the invention is made of a porous polymer material, especially of perfluoro-polymers and fluoropolymers. In particular, it may be selected from the group consisting of fluorinated ethylene-propylene (FEP) copolymer, polytetrafluoro-ethylene (PTFE), tetrafluoroethylene-hexafluoropropylene-vinylidene fluoride (THV), perfluoro-alkoxyalkane (PFA), sulfonated PTFE (NAFION), or another group polyethylene, a cellulose derivative, polyamide, poly (methyl methacrylate). In one embodiment of the invention, the porous support according to the invention can be embodied as a membrane or flat molded part (frit).

The support has a pore volume and can be prepared in one of different ways. Suitable methods include, in particular, sintering methods in which a particulate or fibrillary polymer material is pressed to a shape with heating. In particular, methods used for preparing non-wovens or web technologies can be employed for preparing fibrillary material. For particulate material, methods used for preparing frits are suitable, in particular. In addition, pore-producing methods are suitable, such as, in particular, the expansion of a starting material by volatile blowing agents (foaming) or by soluble sacrificial materials that are leached out of the pores before the support is used. In addition to such material-transforming method, those methods in which pore formation takes place during the deposition of a solid phase from a solvent, such as hydrogel-cryogel or aerogel methods, are also suitable.

In one embodiment, the support is prepared by sintering from spherical PMMA particles having a diameter of 40 μm. When cells are bound to the surface by means of immobilized antibodies and stained with an antibody-fluorescent dye conjugate, particularly brilliant images are obtained if an approximation of the refractive indices is realized by displacing the aqueous phase by, for example, a mixture of 83% thiodiglycol and 17% water.

In another embodiment, the support is prepared from a non-woven made from spun FEP. In this case, the adaptation of the refractive indices is achieved already if usual buffering media, such as PBS, are used.

If no functional groups for the chemical coupling of binding molecules are present on the surface of the porous material intended for the support, the latter can be functionalized by chemical reactions with suitable means in order to immobilize the binding molecules required for the heterogeneous binding assay to be performed to the porous support.

Thus, for example, porous supports formed as a membrane can be provided with a hydrophilizing coating of polyvinyl alcohol methacrylate (PVMMA(2.5)) according to DE-A-10 2009 003374, "Permanent Hydrophilic Porous Coatings Onto a Substrate and Porous Membranes Thereof", paragraph 0061 and Table 1.

A PTFE membrane thus hydrophilized by OH groups can be further reacted with 3-aminopropyltriethoxysilane in an organic solvent, for example, and thus provided with amino groups. These may be reacted, for example, with a homobifunctional N-hydroxysuccinimide ester, in order that binding molecules can be coupled thereto, as described in the handbook of Affinity Chromatography (2006), Vol. 92, Taylor & Francis, edited by David S. Hage, pp. 54-55. The use of succinic acid as a bifunctional spacer is particularly advantageous.

Membranes of hydrophilized PTFE (OMNIPORE JC of Millipore) to which antibodies were coupled in the way described have proven particularly favorable. Typical degrees of modification are within a range of from 1 to 100 μg of antibody, especially 5-10 μg of antibody, per 100 μl of membrane volume. At a membrane thickness of 50 μm, the upper value of this optimum range corresponds to about 4 μg of antibody per cm$^2$ of filter area with up to about $3 \times 10^{13}$ specific binding sites. Since the coupling yields in this process are typically within a range of 1-10%, about $0.3-3 \times 10^{12}$ active binding sites/cm$^2$ can be assumed in such a membrane. With such a density of binding molecules, it is very well possible to bind microorganisms or characteristic fragments thereof biospecifically to the membrane, especially if the antibodies are directed against antigens that occur several times on the membrane, such as polysaccharides or lipopolysaccharides.

The invention is further illustrated by means of the following Examples.

EXAMPLE 1

Fluorimetric Detection of *Legionella* Bacteria in Drinking Water

1. Functionalization of a PTFE Membrane and Antibody Immobilization

In a first step, a PTFE membrane hydrophilized with OH groups (OMNIPORE JC from Millipore) was aminated by treatment with 3-aminopropyltriethoxysilane (APTS). Thus, 50 μl of 3-aminopropyltriethoxysilane (Sigma-Aldrich Chemie GmbH) was dissolved in 4950 μl of acetone, and applied to the dry membrane (d=5 cm) in a 90 mm glass Petri dish. The Petri dish was transferred to a glass desiccator, which was evacuated quickly (<10 min) to <300 mbar. It was incubated in the closed desiccator on an orbital shaker at 20 rpm at room temperature for 12 hours. Subsequently, 0.42 μl of reagent grade 37% hydrochloric acid (Carl Roth GmbH & Co. KG) was added. The Petri dish was then transferred to a glass desiccator, which was evacuated quickly (<10 min) to <300 mbar. It was then incubated in the closed desiccator on an orbital shaker at 20 rpm at room temperature for 6 hours. Thereafter, the liquid was discarded by suction, and 6.25 ml of acetone was added to the membrane. Thereafter, the desiccator was closed again, and the dish was shaken on an orbital shaker at 40 rpm. Each of these steps was repeated twice. Finally, the membrane was dried at room temperature for at least 1 hour with sufficient supply of air.

In the second step, the COOH functionalization of the membrane was performed. Thus, the dried membrane in a Petri dish was covered with a layer of 5 ml of DMF and shaken on an orbital shaker for 5 min. The liquid was discarded by suction, and the previous step was repeated. The liquid was again discarded by suction.

Thereafter, the membrane was covered with a layer of 5 ml of succinic acid anhydride solution (400 mg in 10 ml of DMF) and shaken on an orbital shaker for 10 min. Subsequently, 5 μl of pyridine was added, and the dish was incubated in the closed desiccator with desiccant on an orbital shaker at 20 rpm at room temperature for 12 hours. The liquid was discarded by suction, and the membrane was covered with a layer of 5 ml of bidistilled water. The membrane was shaken on an orbital shaker for 5 min. The two previous steps were repeated.

In the third step, the coupling of antibodies to the membrane was effected:

Thus, the wet membrane from step 2 was covered with a layer of 5 ml of MES buffer (0.05 M solution of 19.5 g of 2-(N-morpholino)ethanesulfonic acid in 1 liter of H$_2$O, pH=5.5), followed by shaking on an orbital shaker for 5 min. The previous step is repeated. The liquid was discarded by suction, the membrane was covered with a layer of 5 ml of EDC solution (328.6 mg of 1-ethyl-3-[3-dimethylaminopropyl]carbodiimide hydrochloride in 20.53 ml of MES powder), and shaken on an orbital shaker for 10 min. Thereafter, 0.5 ml of sulfo-NHS solution (406.2 mg of N-hydroxysulfosuccinimide, 1.127 ml of MES buffer) was added, and after an incubation time of 30 min, the liquid was sucked off, and the membrane was covered with a layer of 5 ml of MES. It was then shaken on an orbital shaker for 10 min. The two previous steps were repeated. Subsequently, the membrane was covered with a layer of 2.5 ml of antibody solution (80 μg/ml of anti-*Legionella* antibody 5F4, Senova GmbH, Weimar, in MES buffer), and shaken on an orbital shaker for 120 min. The liquid was again discarded by suction, and the membrane was covered with a layer of 5 ml of MES including 0.25% ethanolamine solution (blocked) for 30 minutes. The liquid was subsequently discarded, and the membrane was covered with a layer of 5 ml of MES buffer, followed by shaking on an orbital shaker for 10 min. The preceding step was repeated.

Finally, the liquid was discarded by suction, and the membrane was covered with a layer of 5 ml of drying buffer, followed by shaking on an orbital shaker for 60 min. The liquid was discarded by suction, and the membrane was dried at room temperature with forced air circulation for 1 hour.

2. Preparation of the Filter Assembly

Circular filters having a diameter of 1 to 5 mm were punched out of the membrane using a punch. The filters were placed on a polyethylene frit 2 (Durst Filtertechnik, Besigheim, Germany, type XM112, d=5 mm, h=1.6 mm), and introduced into the cavity of a sample holder of acrylic glass. Above the membrane, a short piece of PTFE flexible tube 3 was pressed into the cavity, and the Luer port 4 of a minicolumn (750 μl ABICAP, Senova GmbH, Weimar) was inserted into flexible tube 3. FIG. 1 shows an assembly as used in Example 1.

Figure 2:
FIGS. 2 to 4 show microphotographs of a membrane section.

3. Application of Samples, Staining with Anti-*Legionella*-Phycoerythrin, and Optical Evaluation In a first step, 500 μl of the sample to be examined was pipetted into the minicolumn. After the sample had flowed by gravity through the assembly, 750 μl of washing buffer (0.1% BSA and 0.05% Tween 20 in PBS buffer, pH=7.4) was pipetted into the Abicap column. After the washing buffer, 500 μl of a 0.5 μg/ml solution of anti-*Legionella*-phycoerythrin conjugate (ImmunoTools GmbH, Rostock, Germany) in casein-containing (1 mg/ml) PBS buffer, pH=7.4, was added in a second step. After the conjugate solution had flowed through the assembly in about 4 min, a washing step with 750 μl of washing buffer was performed three times. Subsequently, the Abicap column and the PTFE flexible tube were removed, and the membrane was covered with a layer of a few μl of physiological saline. Using an epifluorescence microscope (Axiostar plus with light source HXP150C, set of filters 43 HE, objective A-Plan 10×/0.35; all from Zeiss MicroImaging GmbH, Jena, Germany) and a microscope camera (AxioCam MRc5, Zeiss MicroImaging GmbH, Jena, Germany), the fluorescence-labeled germs on the transparent membrane were counted. With this method, a detection limit of 10 germs per filter was reached. FIG. 2 shows a microphotograph of a membrane section according to Example 1. The applied sample contained about 500 *Legionella* bacteria.

EXAMPLE 2

Detection of *Legionella* Bacteria in Drinking Water by Means of HRP/TMB$_{Prec}$ Detection 1. Antibody Immobilization on an HDPE Membrane In a first step, anti-*Legionella* antibodies (5F4, Senova, Weimar) were immobilized by physisorption on an HDPE membrane (Porex Inc. type T3, pore size 5-10 μm, thickness 200 μm, high density polyethylene=HDPE) by a method analogous to that described in Meyer M. F. et al., Biosensors and Bioelectronics 2007, 22 (6), p. 973. Thus, 50 circular filters, d=5 mm, were punched out, placed into a 50 ml beaker with 20 ml of ethanol (96%), and degassed in a desiccator under 10 Torr with slight stirring on a magnetic stirrer for 20 min. Subsequently, the filters were washed with 50% ethanol solution, and finally degassed three times in 10 ml of carbonate buffer (100 mM, pH 9.5). Subsequently, 100 μl of a 1 mg/ml anti-*Legionella* solution in carbonate buffer was added with stirring. The filters were incubated in a desiccator at room temperature with slight stirring for 6 hours. Subsequently, the antibody solution was replaced by a block solution, 5.5 mg/ml of casein in PBS buffer (150 mM, pH=7.3), and after degassing, was blocked with stirring for 1 hour. Subsequently, the block solution was replaced by drying buffer (PBS, 1% BSA, 1% sucrose), and incubated in a desiccator for 1 h. Finally, the membranes were dried at room temperature in a fluidized-bed drier (FPD200 Endicots, UK) for 15 min.

2. Preparation of the Filter Assembly

The preparation of the filter assembly was effected by analogy with Example 1, item 2.

Figure 3A:
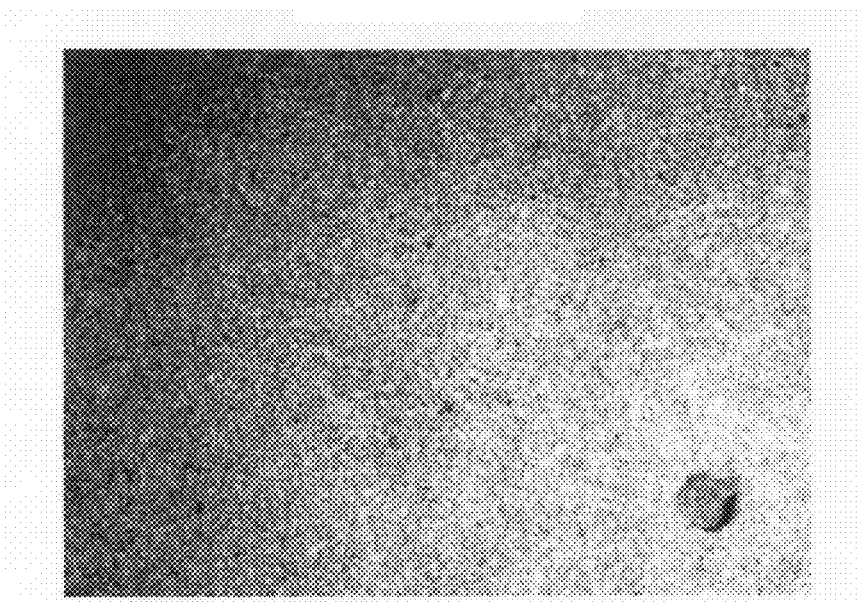
Figure 3B:
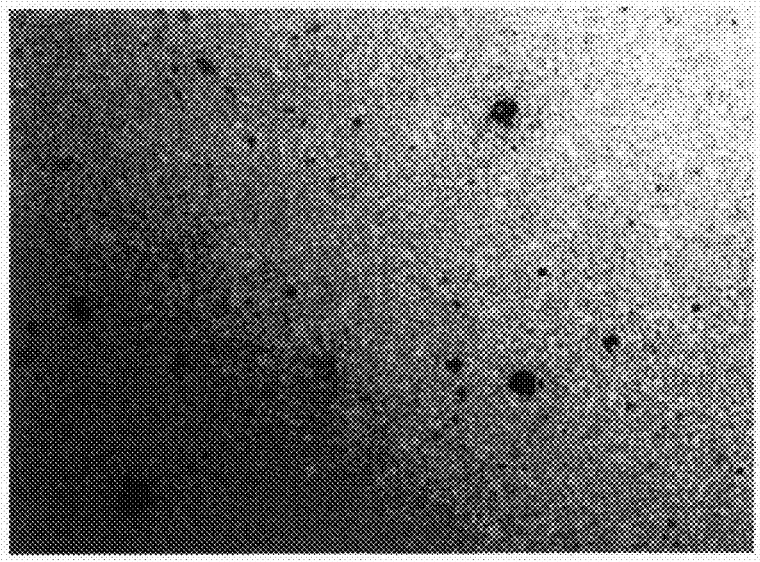
Figure 3C:
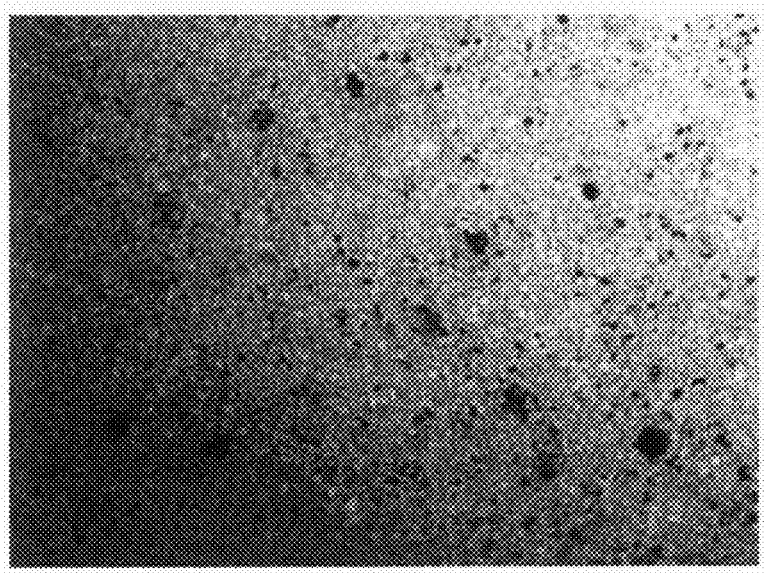

3. Application of Samples, Staining with Anti-*Legionella*-HRP Conjugate+Precipitating TMB, and Optical Evaluation In a first step, 2×500 μl each of sample solution with concentrations of 10 cfu/ml, 100 cfu/ml, 1000 cfu/ml was pipetted into the assembly. Subsequently, 750 μl of PBS washing buffer and thereafter 500 μl of a 5 μg/ml solution of anti-*Legionella*-peroxidase conjugate in PBS buffer (Senova GmbH, Weimar, Germany) was added. After the conjugate solution had flowed through the assembly, 3×750 μl of washing buffer and subsequently 500 μl of a precipitating TMB substrate solution (SDT company, Baesweiler, Germany) were pipetted into the assembly. After 4 minutes, 750 μl of washing buffer was again pipetted onto the column for quenching the detection reaction. Subsequently, the membrane was removed, transferred onto a microscope slide, and the characteristic color halos of the germs were counted using a transmitted light microscope (Axiostar plus with a halogen light source and objective A-Plan 5×/0.12; all from Zeiss MicroImaging GmbH, Jena, Germany) and a microscope camera (AxioCam MR3, Zeiss MicroImaging GmbH, Jena, Germany). FIG. 3 shows microphotographs obtained thereby of sections of the membrane for different *Legionella* contents of the sample. With this method, it is possible to reach detection limits within a range of 5-15 cells. FIG. 3*a* shows a microphotograph of a membrane section according to Example 2. The applied sample contained no *Legionella* bacteria. FIG. 3*b* shows a microphotograph of a membrane section according to Example 2. The applied sample contained about 100 *Legionella* bacteria. FIG. 3*c* shows a microphotograph of a membrane section according to Example 2. The applied sample contained about 1000 *Legionella* bacteria.

EXAMPLE 3

Detection of *Salmonella* Bacteria by Live Staining on a Transparent Membrane

1. Immobilization of the Antibody

A membrane according to Example 1, item 1, was used. Instead of the antibody employed there, monoclonal anti-*Salmonella* spp. antibodies (1E6, Sifin GmbH, Berlin) were immobilized on the membrane.

2. Preparation of the Filter Assembly

Circular filters having a diameter of 24 mm were punched out of the membrane using a punch. The filters were fixed to the bottom of an empty 20 ml column with insertable bottom (SpinColumn, AHN Biotechnology, Nordhausen, Germany). A peristaltic pump was connected to the lower Luer port of the column.

3. Sample Preparation 25 g of a heat-sterilized meat sample and 225 ml of buffered peptone water were added into the inner filter bag of a Stomacher bag (BA6141/STR, Seward Limited, UK), and inoculated with 10 μl of a *Salmonella typhimuria* (ATCC 14028) preculture (1000 germs/ml). The sample was subsequently incubated at 37° C., and 10.1 ml each of the sample was removed from the outer bag after 4, 6, 8 and 10 hours.

4. Reference Examination

100 μl of each subsample was plated onto XLD agar. After incubation at 37° C. for 24 hours, the number of colonies was determined by counting.

5. Application of Samples, Staining, and Optical Evaluation

Immediately after being removed from the Stomacher bag, 10 ml of the subsample was added into the column and drawn off through the peristaltic pump at a flow rate of 1 ml/min. After the filtrate was completely removed from the flexible tube of the pump, the direction of flow of the pump was reversed, and 5 ml of washing buffer was pressed through the membrane into the column at a flow rate of 1 ml/min. The supernatant formed thereby in the column was discarded. In a second step, the original direction of flow was restored, and 5 ml of LIVE/DEAD BacLight (Invitrogen, Carlsbad, U.S.A.) was added into the column, and drawn off through the peristaltic pump at a flow rate of 0.5 ml/min. Subsequently, 5 ml of physiological saline was added into the column, and drawn off through the peristaltic pump at a flow rate of 2 ml/min. In the last step, the membrane was removed from the column, transferred onto a microscope slide, covered with a layer of physiological saline, which was covered by a cover slip. Using an epifluorescence microscope (Axiostar plus with light source HXP150C, sets of filters 14 and 38 HE, objective A-Plan 10×/0.35; all from Zeiss MicroImaging GmbH, Jena, Germany) and a microscope camera (AxioCam MRc5, Zeiss MicroImaging GmbH, Jena, Germany), two crosswise arranged regions of the membrane of 1.4 mm×20 mm and 20 mm×1 mm, respectively, were examined. The fluorescence-labeled germs were counted and classified using the different fluorescent colors.

6. Comparison of the Examination Methods

On the membrane segment (=$\frac{1}{12}$ of the total area), the following numbers of viable germs were counted, and the number of germs per ml of sample was calculated therefrom:

|  | Incubation time | | | |
| --- | --- | --- | --- | --- |
|  | 4 hours | 6 hours | 8 hours | 10 hours |
| Number of green fluorescent cells | 5 | 119 | 1620 | >10,000 |
| Calculated number of cells per ml | 4 | 94 | 1300 | Y 7,900 |

The following numbers of colony-forming units (cfu) were determined by plating, from which the number of germs per ml of sample was calculated:

| Number of colonies | 0 | 8 | 141 | Cell lawn |
| --- | --- | --- | --- | --- |
| Calculated number of cells per ml | 0 | 80 | 1410 | — |

A good agreement between the methods was found, the membrane method yielding a positive result in terms of *Salmonella* load as quickly as after four hours of incubation.

EXAMPLE 4

Detection of T Lymphocytes on PTFE Membrane by Immunofluorescence Staining

1. Immobilization of the Antibody

An FEP membrane (TITK Rudolstadt, Germany) modified with OH groups in accordance with DE-A-10 2009 003374 and having a pore size of about 40 µm is used as the support. The membrane was prepared by analogy with Example 1.1. Instead of the antibodies employed there, 80 µg/ml monoclonal anti-CD3-IgG (eBioscience, San Diego, U.S.A.) was immobilized.

2. Preparation of the Filter Assembly

The filter assembly from Example 1.2 was adopted.

3. Application of Samples, Staining, Optical Evaluation, and Comparison with Reference Method 10 µl of heparinized capillary blood was diluted with 2 ml of PBS buffer (150 mM; pH=7.4). In a first step, 250 µl of the sample was pipetted into the Abicap column. After the sample had flowed by gravity through the assembly, 750 µl each of washing buffer (0.1% BSA and 0.05% Tween 20 in physiological saline) was pipetted three times into the Abicap column, and 500 µl of a 0.5 µg/ml solution of anti-CD3-phycoerythrin conjugate (Cat No. 12-0039, eBioscience, San Diego, U.S.A.) in PBS blocking buffer (150 mM, pH=7.4, casein (1 mg/ml) was added. After the conjugate solution had flowed through the assembly in about 4 min, a washing step with 750 µl of washing buffer was performed three times. Subsequently, the Abicap column and the PTFE flexible tube were removed, and the membrane was covered with a layer of a few µl of physiological saline. Using an epifluorescence microscope (Axiostar plus with light source HXP150C, set of filters 43 HE, objective A-Plan 10×/0.35; all from Zeiss MicroImaging GmbH, Jena, Germany) and a microscope camera (AxioCam MRc5, Zeiss MicroImaging GmbH, Jena, Germany), the fluorescence-labeled cells on the membrane were counted. 1800±200 cells were found, which corresponds to a cell count of $1.4 \times 10^6$/ml. From an identical blood sample, the number of T lymphocytes was determined to be $1.62 \times 10^6$/ml using a clinical flow cytometer (Beckman-Coulter GmbH, Krefeld, Germany).

EXAMPLE 5

Detection of Cells in the Entire Depths of the Support

Figure 4A:
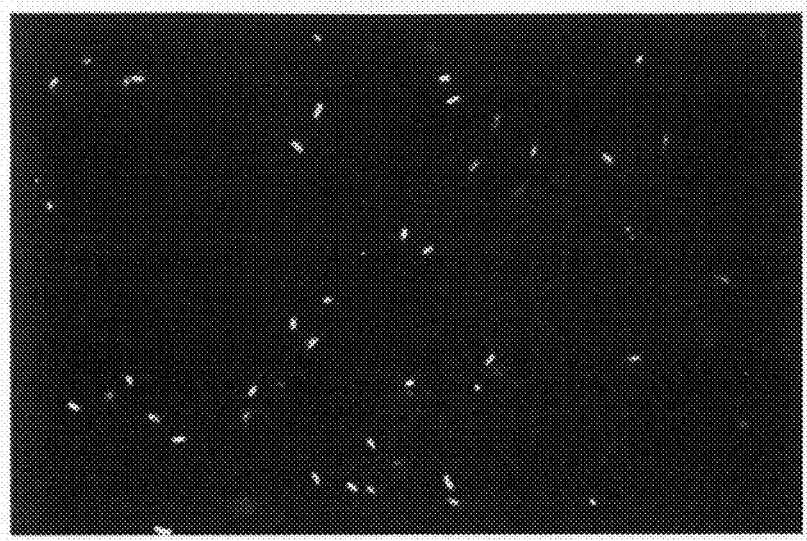
Figure 4B:
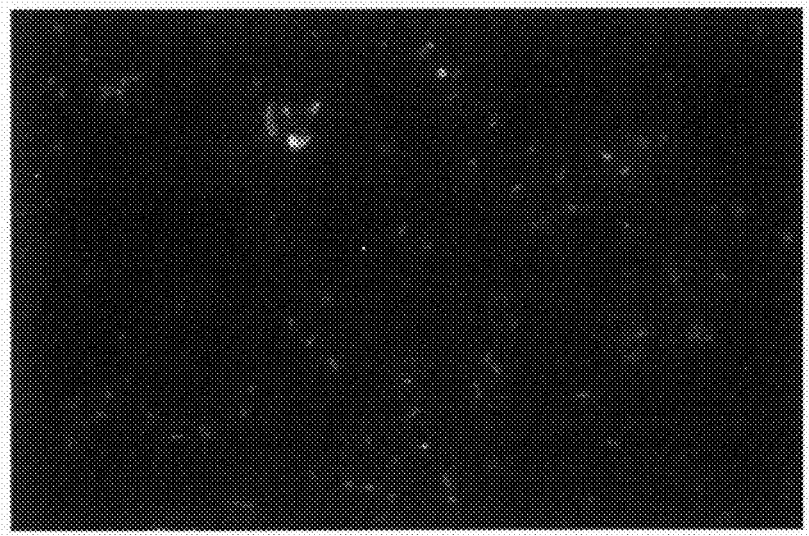

A membrane was prepared as described in Example 1, and the experiment from Example 1 was performed with a suspension of *Legionella* bacteria with 10,000 germs/ml as the sample. Using an epifluorescence microscope (AxioVert star 200 with light source HBO100, set of filters 43 HE, objective A-Plan 20×/0.45; microscope camera AxioCam MRc5, Zeiss MicroImaging GmbH, Jena, Germany), 20 fluorescence images were prepared of a representative detail of the membrane. Between the individual images, the membrane was shifted along the optical axis by 5 µm each, and thus a focus stack through the entire depth of the membrane was prepared. FIG. 4a shows a detail of an image whose focal plane is near the front surface of the membrane. In an image-processing program (AxioVision, Zeiss MicroImaging GmbH, Jena, Germany), an averaged image with a normalized contrast range was prepared by adding up the individual pictures pixel by pixel. FIG. 4b shows the detail of this averaged image that is congruent with FIG. 4a. Comparing the two images, it becomes clear that objects that only produce weak color fogging in the individual image are also recognizable in high definition in the averaged image.

The invention claimed is:

1. A process for detecting cells from a sample, comprising the following steps:
    (a) applying the sample or a fraction of the sample in liquid phase in a direction of flow to a porous two-dimensional support having an entire volume with pores having on the surface thereof at least one binding molecule specific for the cells to be detected or for fragments thereof;
    whereby the cells to be detected or fragments thereof enter into the pores of said porous support, said pores having a mean pore size that allow entry of the cells or fragments thereof into the pores, whereby the cells or fragments to be detected are retained in the entire support volume by binding to the at least one binding molecule specific for the cells or fragments to be detected; and
    (b) performing an optical read-out by high definition imaging the entire porous support volume using an optical system having an optical axis, wherein the optical axis of the optical system runs in the direction of flow.

2. The process according to claim 1, wherein said support is washed before the performing step, after the sample or fraction of sample has been applied and the cells or cell fragments to be detected have entered the pores.

3. The process according to claim 1, wherein said sample is subjected to a sample treatment before the performing step to label said cells or fragments.

4. The process according to claim 3, wherein said labeling is effected by staining using a dye.

5. The process according to claim 1, wherein said porous support is a porous membrane.

6. The process according to claim 1, wherein said optical read-out is effected by a microscopic method.

7. The process according to claim 1, wherein each of said cells or cell fragments to be detected is a microorganism.

8. The process according to claim 7, wherein said microorganism is selected from the group consisting of *Salmonella* spp., *Claviceps* spp., *Lister* spp., *E coli*, non-*E. coli* coliform germs, *Campylobacter* spp., *Bacillus cereus*, sulfite-reducing clostridia, and coagulase-positive staphylococci.

9. The process according to claim 1, wherein said binding molecule specific for the cells or cell fragments to be detected is selected from the group consisting of antibodies, lectins, bacteriophages, and specific binding factors.

10. The process according to claim 1, wherein said porous support is made of foamed, sintered or fibrous inorganic or organic materials.

11. The process according to claim 1, wherein said cells or cell fragments to be detected are rendered detectable by live/dead staining.

12. The process according to claim 1, wherein said cells or cell fragments to be detected are rendered detectable by binding a conjugate of an antibody and an enzyme or a dye or colorant particle.

13. The process according to claim 1, wherein said cells or cell fragments to be detected are rendered detectable by binding a conjugate of an antibody and an enzyme.

14. The process according to claim 1, wherein said cells or fragments to be detected are rendered detectable by binding a nucleic acid probe.

15. The process according to claim 1, wherein said reading out is performed by photometry, luminometry, or fluorometry.

16. The process according to claim 1, wherein the difference between indices of refraction, $n_f - n_p$, of a medium filling the pores of said porous support, $_p$, and that of the porous support, $n_f$, is smaller than 0.05.

17. The process of claim 1, wherein the porous support is a porous membrane having a thickness of 0.05-1 mm.

* * * * *